United States Patent [19]

Masreliez

[11] 4,177,799
[45] Dec. 11, 1979

[54] DENTAL PULP TESTER

[76] Inventor: Carl J. Masreliez, 3301 - 181st Pl. NE., Redmond, Wash. 98052

[21] Appl. No.: 818,737

[22] Filed: Jul. 25, 1977

[51] Int. Cl.$^2$ .............................................. A61B 5/05
[52] U.S. Cl. ................................. 128/741; 128/776; 128/787; 32/40 R; 433/27
[58] Field of Search ............ 128/2 N, 2 R, 2 S, 2.1 R, 128/2.1 C, 2.1 M, 2.1 Z, 303.13, 303.14, 303.17, 303.18, 405, 406, 409, 410, 411, 419 R, 421, 422, 423; 32/40 R

[56] References Cited

U.S. PATENT DOCUMENTS

| | | | |
|---|---|---|---|
| 2,204,295 | 6/1940 | Brockman | 128/2.1 R |
| 2,522,052 | 9/1950 | Logan et al. | 128/2.1 R |
| 2,949,107 | 8/1960 | Ziegler | 128/2.1 R |
| 3,128,759 | 4/1964 | Bellis | 128/2.1 R |
| 3,295,514 | 1/1967 | Hein et al. | 128/2.1 R |
| 3,478,744 | 11/1969 | Leiter | 128/303.14 |
| 3,755,900 | 9/1973 | Friedman | 128/2.1 R X |
| 3,794,022 | 2/1974 | Nawracaj et al. | 128/422 |

FOREIGN PATENT DOCUMENTS

| | | | |
|---|---|---|---|
| 119482 | 8/1966 | Czechoslovakia | 128/2.1 R |
| 897961 | 6/1962 | United Kingdom | 128/303.14 |
| 1298423 | 12/1972 | United Kingdom | 128/2.1 R |

*Primary Examiner*—Lee S. Cohen
*Attorney, Agent, or Firm*—Seed, Berry, Vernon & Baynham

[57] ABSTRACT

A system for testing the dental pulp of a tooth by electrically stimulating the pulp with a pulsating signal having a continuously increasing amplitude. The system includes a probe having an electrode adapted to the tooth, and a contact device for sensing when the probe electrode makes contact with the tooth and for increasing the amplitude of the stimulus from an initial value. The intensity continues to increase as long as the probe electrode is in contact with the tooth. The electrical stimulus may be generated by a voltage controlled pulse generator driving the primary of a transformer, with the secondary of the transformer connected to the electrode probe. The transformer has a relatively low cutoff frequency so that the amplitude of the signal across the secondary is proportional to the pulse width of the incoming signal. Consequently, as the control voltage to the voltage control pulse generator increases, the amplitude of the pulses across the secondary also increases. The voltage control pulse generator also drives a counter, and the output of the counter is indicated on a digital display. Since the amplitude of the control voltage is a function of the number of pulses generated by the pulse generator, the output of the counter indicates the amplitude of the electrical stimulus. Alternatively, a ramp generator is connected to one end of the primary and the other end of the primary is periodically grounded responsive to fixed frequency, fixed duration pulses from the output of an oscillator.

25 Claims, 5 Drawing Figures

U.S. Patent   Dec. 11, 1979   Sheet 1 of 2   4,177,799
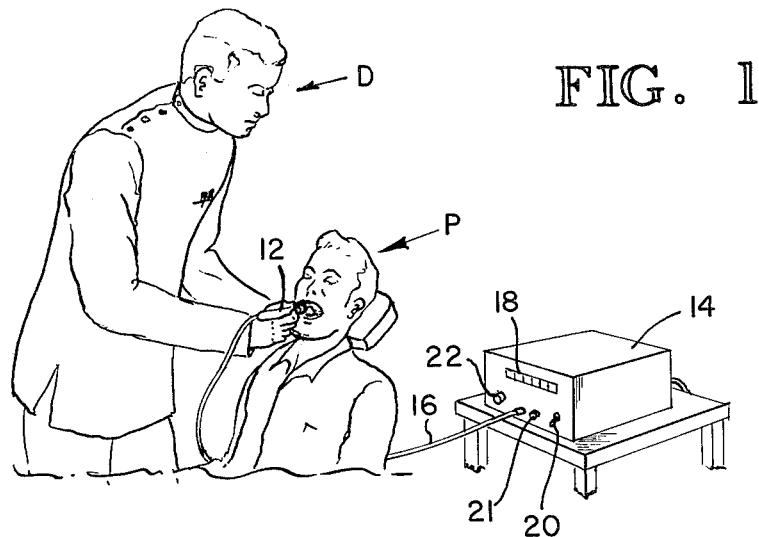
FIG. 1
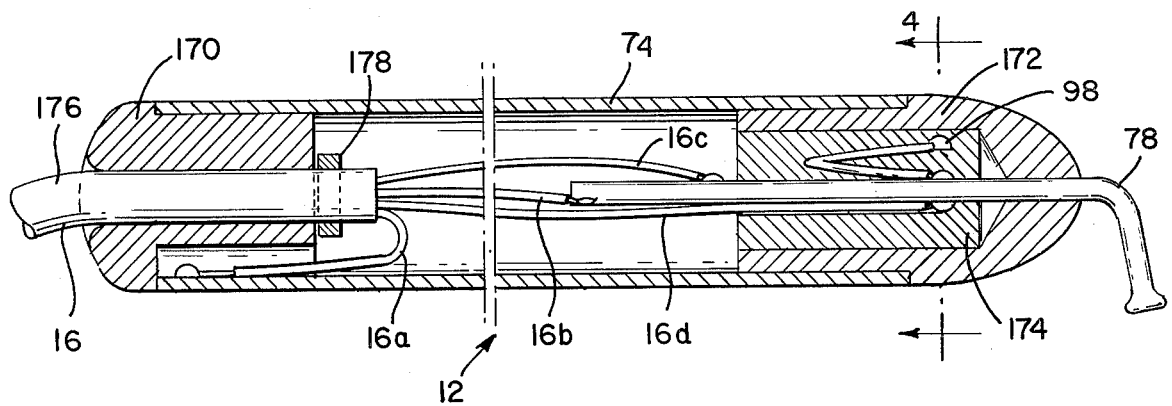
FIG. 3
FIG. 5
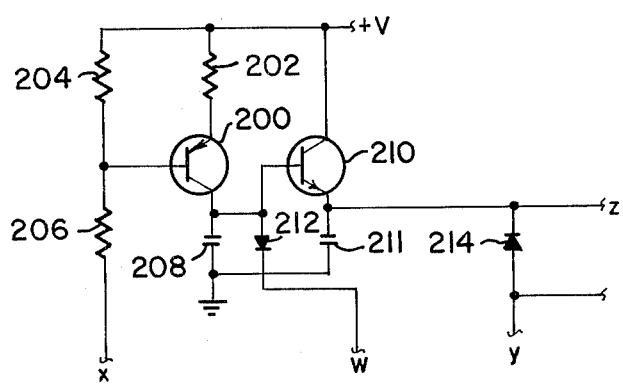
FIG. 4
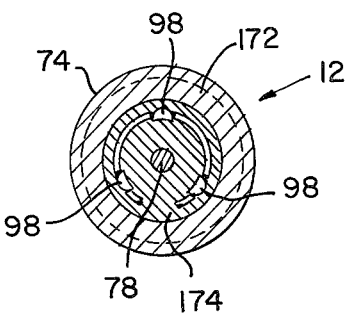

DENTAL PULP TESTER

BACKGROUND OF THE INVENTION

1. Field of the Invention

This invention relates to dental pulp testers, and, more particularly, to a pulp tester for automatically producing an increasing intensity electrical stimulus upon contact of a dental probe with a tooth, and for displaying the intensity of the electrical stimulus at the time the probe is removed from the tooth.

2. Description of the Prior Art

When a tooth has been subject to decay, physical trauma, thermal changes or irritation by sweet foods or deep fillings, the pulp tissue becomes inflamed. When this inflammation is left untreated for a long time, the ensuing pulpal inflammation generally proceeds to a severe infection with abscess formation about the root tips. It is at this stage that many teeth require extraction and that endodontic procedures, designed to help remove this infection, are least successful.

Electric devices used to test the vitality of pulpal tissue have long been used as diagnostic aids by dentists. For example, these devices have found application where a patient complains of pain on one side of the mouth and cannot isolate the specific tooth from which the pain emanates. Also they have been used in the diagnosis of decay which develops around the borders of fillings in teeth with existing restorations—a situation where x-rays alone may not indicate the presence or extent of the decay.

In actual operation, a stimulating electrode of an electric pulp tester is applied to a tooth which is undergoing examination. The operator then gradually raises the level of the voltage at the electrode until the patient feels a tingling or mild electric shock in the tooth that is being touched by the electrode. By comparing the voltage level to which the patient responds with the level at which other of his normal teeth respond, the dentist can make a diagnosis on the state of inflammation or vitality of the dental pulp in the tooth under examination.

While the existing dental pulp testers have proved to be valuable diagnostic tools, they suffer from certain disadvantages which have limited their utility. The principal disadvantage of such testers has been the speed at which they can be used. Conventional pulp testers produce an electrical stimulus which it is manually switched to an on condition, and which is subsequently manually increased. Consequently, it is necessary for a dentist to divert his attention from the patient to the pulp tester in order to increase the intensity of the stimulation. Some conventional pulp testers have attempted to minimize this problem by placing the intensity control on the probe itself, but it is still necessary for the dental practitioner to direct his attention away from the patient to this control. An additional factor in decreasing the speed at which conventional pulp testers may be used is the difficulty in reading their display devices. Generally, these displays are rotary or sliding controls which require the practitioner to interpret the position of the control dial with respect to a fixed mark, and then record the stimulus reading corresponding to the position of the control dial. Although approximate readings can be obtained fairly rapidly, it is very difficult to accurately interpret such displays at a fairly rapid rate.

Another disadvantage of conventional pulp testers is that a reasonable testing rate can only be achieved by rapidly increasing the intensity of the stimulation. However, this rapid increase causes the intensity to "overshoot" the point where the patient can perceive the stimulation before the probe can be removed from the tooth and the increase in intensity can be terminated. Consequently, the patient is subjected to unnecessary pain, and the intensity readings taken from the display are erroneously high.

Still another disadvantage of conventional pulp testers is the characteristics of the electrical stimulus which they apply to a tooth. The electrical stimulus is generally either a continuous voltage having a magnitude which increases with time, or a continuous series of pulses having an amplitude which increases with time. As the dental pulp is stimulated the tooth loses some of its sensitivity until the stimulus is removed and the pulp nerves are "reset". Since these conventional stimulus forms do not allow the pulp to become reset during a test, the level of stimulus required for the patient to perceive the stimulus is unduly high.

In summary, conventional pulp testers are inherently inaccurate, and they are incapable of being used at a relatively fast rate.

SUMMARY OF THE INVENTION

It is an object of the invention to provide a dental pulp tester which is capable of rapidly and accurately measuring the condition of dental pulp.

It is another object of the invention to provide a dental pulp tester which does not require the manipulation of any operating controls during use.

It is still another object of the invention to provide a dental pulp tester which increases the intensity of the electrical stimulation in a manner which allows the dental pulp to become reset during a test so that the stimulus is perceived at its lowest possible level.

It is a further object of the invention to provide a dental pulp tester having a display for indicating the intensity of the electrical stimulation which is highly accurate and which may be easily and quickly read.

These and other objects of the invention are accomplished by a dental pulp tester having contact detection means for sensing when the electrode of a dental probe makes contact with the tooth under test. The contact detection means causes the intensity of the stimulus to increase from a low initial level until the probe is removed from the tooth. The intensity of the stimulus when the probe is removed from the tooth is then displayed on a digital display. When the probe once again makes contact with a tooth the display is reset to the initial value of intensity, and the intensity of the stimulus increases from the initial value. The stimulation is in the form of intermittently produced bursts of pulses with the amplitude of each burst being larger than the amplitude of the previous burst. Consequently, the dental pulp is allowed to reset before each increase in the intensity of the stimulus.

BRIEF DESCRIPTION OF THE DRAWINGS

FIG. 1 is an isometric view of the dental pulp tester in use.

FIG. 3 is a cross-sectional view of the dental probe of the dental pulp tester.

FIG. 4 is a cross-sectional view taken along the line 4—4 of FIG. 3.

FIG. 5 is a schematic of a second embodiment of the dental pulp tester.

DETAILED DESCRIPTION OF THE PREFERRED EMBODIMENTS

Figure 2:
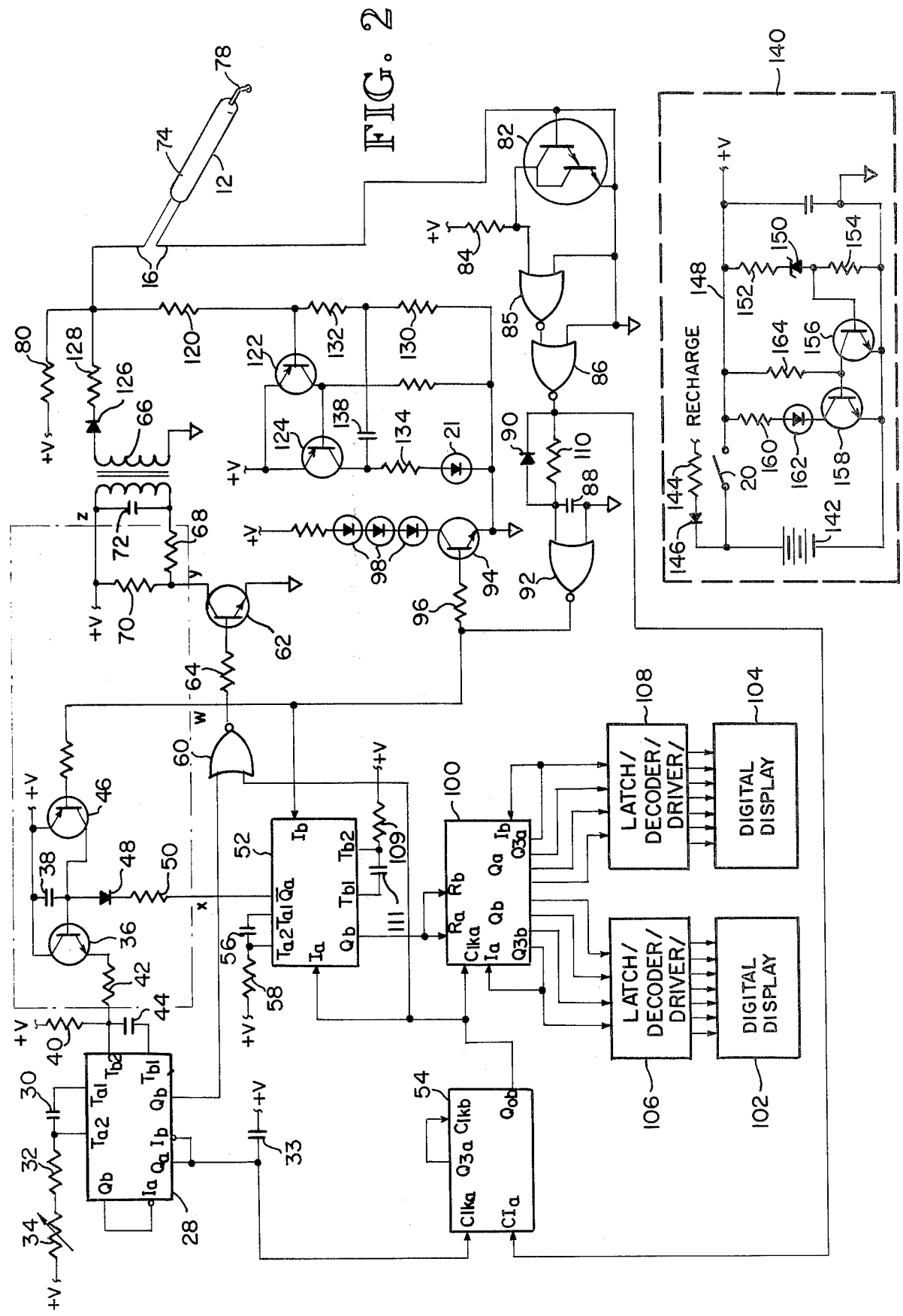
FIG. 2 is a schematic of a first embodiment of the dental pulp tester.

The dental pulp tester is used to test the dental pulp in the teeth of a patient P as illustrated in FIG. 1. The dental practitioner D utilizes a probe 12 having an electrode contacting a tooth under test. The electrode 12 is connected to a testing unit 14 through electric conductors 16. The testing unit 14 includes a digital display 18 which provides an indication of the intensity of the electrical stimulus from the probe 12. The only controls and indicators for the unit are an on-off switch 20, a low-voltage warning light 21 which is illuminated if the amplitude of the electrical stimulus falls below a minimum value, and a sweep rate control 22 which adjusts the rate at which the intensity of the stimulus increases. Both of these controls 20,22 normally remain stationary while the dental pulp of a patient P is being tested.

As illustrated in FIG. 2, the electrical stimulus originates in a pulse generator 28 having a pulse width determined by a pulse width control voltage. The voltage controlled pulse generator 28 may be implemented by an integrated circuit dual monostable multi-vibrator or "one-shot" such as a Fairchild F4528 or Motorola MC14528. Basically, the circuit consists of two one-shots 28a, b each having an output $Q_{a,b}$ triggering the input $I_{b,a}$ of the other so that the circuits are periodically triggered. One of the one-shots 28a generates pulses having a manually adjustable duration, while the pulses generated by the other one-shot 28b have a duration determined by a control input. The duration of the pulses from the first one-shot 28a is determined by timing capacitor 30 and the series combination of fixed resistor 32 and variable resistor 34 which is adjusted, as explained hereinafter, to control the rate at which the intensity of the electrical stimulation is increased. A capacitor 33 is connected between supply voltage and the input $I_b$ of the second one-shot 28b in order to trigger the one-shot 28b when power is applied to the unit.

The duration of the pulses produced by the second one-shot 28b is determined by the voltage at the base of transistor 36. Transistor 36 acts as a voltage follower to provide a high impedance discharge path from capacitor 38 to the pulse generator 28. Resistors 40,42 and capacitor 44 are provided to bias the pulse duration at a predetermined value. The capacitor 38 is initially discharged by transistor 46 at the start of each test. Thereafter the capacitor 38 is charged through diode 48 and resistor 50 by periodic, negative going pulses from the $Q_a$ output of a first one-shot 52a in a dual one-shot circuit 52. The first one-shot 52a is triggered at $I_a$ by the $Q_{ob}$ output of decade counters 54b which is driven by the $Q_3$ output of decade counter 54a in series driven by the pulse generator 28. Consequently, the capacitor 38 is incrementally charged for each 20 pulses from pulse generator 28. The duration of the pulse from the one-shot 52, and hence the amount of charge provided during each increment, is determined by timing capacitor 56 and resistor 58.

The $Q_{ob}$ output of the counter 54b also gates the output of the pulse generator 28 through NOR gate 60 to the base of a transistor 62 through resistor 64. Since the output $Q_{ob}$ is alternately low for 10 pulses of pulse generator 28 and then high for 10 pulses of pulse generator 28, NOR gate 60 gates 10 pulses to the transistor 62 and then cuts off the transistor 62 for 10 pulses. Consequently a "dead space" is produced after each burst of 10 pulses which, as explained hereinafter, allows the nerves in the dental pulp to reset after each stimulus so that the nerves are at the maximum sensitivity at the start of each stimulus. As the transistor 62 saturates, current flows through the primary of transformer 66 and resistor 68. Resistor 68 is selected to limit the maximum current flow through the primary of transformer 66. The pulses across the secondary of the transformer, which are generated inductively when turning off the transistor 62, have a peak amplitude which is determined by the value of resistor 70 and the duration of the pulses at the output of the NOR gate 60. Capacitor 72 is provided to dampen the reverse emf spike generated when current flow through transistor 62 is terminated.

In summary, 10 pulses from the pulse generator 28 are gated through the NOR gate 60 to produce 10 equal amplitude pulses across the secondary of transformer 66 followed by a dead space of 10 pulses during which the NOR gate 60 is gated off. After each pulse burst of 10 pulses, the $I_a$ input of one-shot 52a is triggered to generate a charging pulse on the $Q_a$ output of one-shot 52 which incrementally charges capacitor 38 and decreases the control voltage to the pulse generator 28 so that the subsequent burst of pulses from the NOR gate 60 has an increased duration resulting in pulses of increased amplitude across the secondary of the transformer 66. The rate at which the electrical stimulus increases can be varied by adjusting the sweep rate resistor 34 which is controlled by the sweep rate control 22 on the front panel of the unit 14 (FIG. 1).

As explained in greater detail hereinafter, the probe 12 includes a conductive outer sleeve 74 surrounding, and insulated from, an elongated center electrode 78. In operation the center electrode 78 makes contact with the tooth of a patient, and the sleeve 74 is in electrical contact with the patient through the dentist's hand and the patient's lip. The sleeve 74 is connected to the power supply output through resistor 80 so that when the electrode 78 makes contact with the tooth, current flows through resistor 80 and probe 12 into the base of the darlington pair 82. As the darlington pair 82 becomes saturated the current flowing through resistor 84 causes the voltage at the collector of the darlington pair 82 to go low thereby causing the output of NOR gate 85 to go high and the output of NOR gate 86 to go low. The output of NOR gate 86 is connected to the counter inhibit input $CI_a$ of a counter 54a so that as the output of NOR gate 86 goes low counter 54 begins incrementing. At the same time capacitor 88 is discharged through diode 90 so that the output of NOR gate 92 goes high. NOR gate 92 then saturates transistor 94 through resistor 96 and illuminates three light emitting diodes 98 which, as explained hereinafter, are visibly mounted on the probe 12. NOR gate 92 also turns off transistor 46 permitting capacitor 38 to be charged, and it triggers the $I_b$ output of one-shot 52b thereby producing a pulse at the $Q_b$ output which resets counter 100. Counter 100 counts the pulses from the output of counter 54 and displays the contents on digital displays 102,104 through BCD-to-7 segment latch/decoder/drivers 106,108, respectively. The outputs of the counter 100 are continuously displayed until the counter 100 is reset by one-shot 52b. The input $I_b$ of one-shot 52b is connected to the output of NOR gate 92 so that a reset pulse is generated at the output $Q_b$ of one-shot 52b when the output of NOR gate 92 goes high as the probe electrode 78 makes contact with a tooth. The duration of the reset pulse, which is not critical, is determined by the values of timing resistor 109 and timing capacitor 111. The most significant bit output $Q_{3b}$ of the counter 100b is connected to the inhibit input $CI_a$ of counter 100 so the counter 100 "locks up" if incremented to near its maximum capacity.

The tester unit also includes a circuit for insuring that the output voltage from the probe does not fall below a predetermined minimum level. This circuit is connected to electrode 74 through resistor 120. Transistor 122 is normally saturated thereby cutting off transistor 124. When the positive going pulse from the transformer 66 exceeds a level set by the voltage divider formed by resistors 130, 132 in combination with resistor 120, transistor 122 becomes cut off thereby saturating transistor 124 and allowing current to flow in the emitter-collector circuit through resistor 134 and light emitting diode 21. Positive feedback capacitor 138 is provided to completely saturate transistor 124 as transistor 122 goes into cutoff. Consequently, pulsating illumination from light emitting diode 21 indicates that the amplitude of the signal at the output of the transformer 66 is sufficient.

An alternative embodiment of the circuit for generating the electrical stimulus is illustrated in FIG. 5. Basically, the alternative embodiment places a linearly increasing voltage on one lead of the secondary of transformer 66 while the other lead of the transformer secondary is periodically connected to ground through transistor 62 by constant duration pulses from pulse generator 28. The embodiment illustrated in FIG. 5 is placed in the circuit of FIG. 2 with the alphabetical markings of the broken leads matching the correspondingly marked leads illustrated in FIG. 2. The negative going pulses at the $Q_a$ output of one-shot 52 drives transistor 200 into conduction. The current through transistor 200 is proportional to the voltage across resistor 202 divided by the resistance of resistor 202. Resistors 204, 206 form a voltage divider and are selected to place the proper voltage on the emitter of transistor 200 to achieve a predetermined constant current for charging capacitor 208. As capacitor 208 continues to charge a linearly increasing voltage is produced across capacitor 208 which is coupled to output line z by emitter follower transistor 210. Capacitor 211 is provided to filter the output line z which is secondary of transformer 66. Capacitor 208 is reset through diode 212 by a low level output of NOR gate 92 each time the electrode 78 brakes the contact with a tooth. Diode 214 is placed across the secondary of transformer 66 to dampen reverse emf transients which are produced when current through the transistor 62 is terminated. In this alternate embodiment, the probe stimulus output pulses are generated when turning on transistor 62 rather than as in the previous embodiment when turning off transistor 62.

The dental pulp tester unit also includes an internal power supply 140 having a rechargeable battery 142 which may be recharged through resistor 144 and rectifying diode 146. When the on-off switch 20 is in its on position the battery 142 is connected to the power supply line 148. The power supply 140 includes a low-voltage warning circuit which indicates when the battery 142 must be recharged. As long as the voltage on line 148 exceeds the reverse breakdown voltage of zener diode 150 current flows through resistors 152, 154. Under these conditions, transistor 156 is saturated thereby cutting off transistor 158 so that current is unable to flow through resistor 160 and light emitting diode 162. When the voltage on line 148 drops below the breakdown voltage of zener diode 150, transistor 156 is cut off thereby allowing current to flow through resistor 164 and the base-emitter junction of transistor 158. Transistor 158 then saturates allowing current to flow through light emitting diode 162 and indicate that the battery 142 is in need of recharging.

The structure of the probe 12 is best illustrated in FIGS. 3 and 4. The probe 12 includes a cylindrical conductor forming the outer electrode 74 having its ends closed by a pair of end caps 170, 172. The end cap 172 is formed of an insulative, light-transmissive substance such as plastic, and it contains an axial bore which receives the electrode 78 which makes contact with the tooth. A transparent, cylindrical insert 174 placed in a bore formed in the end cap 172 contains the three light emitting diodes 98 which indicate that the electrode 78 has made contact with a tooth as described above. The cable 16 includes a first conductor 16a connected to the outer electrode 74, a second conductor 16b connected to the inner electrodes 78 and a pair of conductors 16c, d completing a circuit with the light emitting diodes 98. The conductors 16 are encased in a cylindrical sheathing 176 which passes through a bore in the end cap 170 and is retained in place by an annular washer 178.

In operation, when the electrode 78 of the probe 12 first makes contact with a tooth the output of NOR gate 86 goes low thereby illuminating light emitting diodes 98, releasing integrating capacitor 38, resetting counter 100 and allowing counter 54 to begin incrementing. When the output of counter 54 goes low the pulses from the output of the pulse generator 28 are gated through NOR gate 60 to drive transformer 66 and generate 10 pulses at the probe 12. The output of counter 54 then goes high thereby gating NOR gate 60 off and triggering a pulse from the $Q_a$ output of one-shot 52a which incrementally charges integrating capacitor 38. When the output of counter 54 again goes low, pulses having an increased duration are gated through NOR gate 60 so that the amplitude of the pulses across the secondary transformer 60 are increased. The pulse bursts continue to increase in amplitude until the electrical stimulus is felt by the patient at which time the electrode 78 is removed from the tooth of the patient. Since the amplitude of the pulses in each pulse burst is incrementally increased after every 20 pulses from the pulse generator 28, the number of pulses counted by counter 100, as indicated by display 102, 104, is an indication of the amplitude of the pulses delivered to the probe 12. When the electrode 78 is removed from the tooth the current path through the probe 12 is broken so that the output of NOR gate 86 goes high thereby charging capacitor 88 through resistor 110. After a predetermined delay time, the output of NOR gate 92 goes low thereby resetting capacitor 38 and extinguishing the light emitting diodes 98. The time delay provided by capacitor 88 and resistor 110 prevents the counter 100 and integrating capacitor 38 from becoming reset should the electrode 78 of the probe momentarily lose contact with the tooth. However, loss of contact between the electrode 78 and the tooth will inhibit the counter 54 to prevent the counter 100 from incrementing and the duration of the pulses from the pulse generator 28 from increasing.

I claim:
1. A system for testing the dental pulp of a tooth, comprising:

a probe having a first electrode adapted to directly contact said tooth;

a second electrode adapted for indirect electrical contact with said tooth;

contact detection means for determining when said first electrode is in contact with said tooth and for generating an initiate signal in response thereto; and electrical stimulus means connected to said probe for producing an electrical stimulus between said first and second electrodes having an intensity which increases responsive to said initiate signal, said electrical stimulus means further including initializing means for resetting the intensity of said electrical stimulus to a predetermined value responsive to termination of said initiate signal for longer than a predetermined period such that the intensity of said electrical stimulus is initialized to a preset value by removal of said first electrode from said tooth for longer than said predetermined period.

2. A system for testing the dental pulp of a tooth, comprising:

a probe having a first electrode adapted to directly contact said tooth;

a second electrode adapted for indirect electrical contact with said tooth;

electrical stimulus means connected to said probe for producing an electrical stimulus between said first and second electrodes having an intensity which increases responsive to an initiate signal;

contact detection means for determining when said first electrode is in contact with said tooth and for generating said initiate signal in response thereto such that the intensity of said electrical stimulus is automatically increased responsive to said first electrode contacting said tooth; and display means operatively associated with said electrical stimulus means for providing an indication of the intensity of said electrical stimulus, said system further including means for retaining said indication of electrical stimulus intensity subsequent to termination of said initiate signal and for automatically removing said indication of electrical stimulus intensity and resetting the intensity of said electrical stimulus to a predetermined value upon subsequent commencement of said initiate signal such that said display means continuously indicates the maximum value of electrical stimulus after said first electrode is removed from said tooth until said first electrode subsequently contacts a tooth.

3. A system for testing the dental pulp of a tooth, comprising:

a probe having a first electrode adapted to directly contact said tooth;

a second electrode adapted for indirect electrical contact with said tooth;

electrical stimulus means connected to said probe for producing an electrical stimulus between said first and second electrodes having an intensity which increases responsive to an initiate signal;

display means operatively associated with said electrical stimulus means for providing an indication of the intensity of said electrical stimulus;

contact detection means for determining when said first electrode is in contact with said tooth and for generating said initiate signal in response thereto such that the intensity of said electrical stimulus is automatically increased responsive to said first electrode contacting said tooth; and contact indication means for producing a visual indication of electrical contact with said tooth, said contact indication means being actuated by said contact detection means and being electrically isolated from said electrical stimulus such that said contact indication means may be actuated prior to generation of said electrical stimulus by said electrical stimulus means.

4. A system for testing the dental pulp of a tooth, comprising:

a probe having a first electrode adapted to directly contact said tooth;

a second electrode adapted for indirect electrical contact with said tooth; and electrical stimulus means connected to said probe for producing an electrical stimulus between said first and second electrodes having an intensity which increases responsive to an initiate signal, said electrical stimulus means further including means for repetitively generating bursts of pulsating signals, the amplitude of said signals being relatively constant during each burst and the amplitude of said signals during each burst being greater than the amplitude of signals during the previous burst.

5. A system for testing the dental pulp of a tooth, comprising:

a probe having a first electrode adapted to directly contact said tooth;

a second electrode adapted for indirect electrical contact with said tooth;

contact detection means for determining when said first electrode is in contact with said tooth and for generating an initiate signal in response thereto;

signal generating means operatively associated with said contact detection means for producing a series of pulses having a pulse duration which increases with time responsive to said initiate signal;

counter means for counting the number of pulses generated by said signal generating means during the period said initiate signal is being produced;

digital display means for displaying the contents of said counter means; and signal processing means having an input connected to said signal generating means and an output connected between said first and second electrodes for producing an electrical stimulus between said electrodes proportional to the duration of said pulses generated by said signal generating means such that the intensity of said electrical stimulus increases with time responsive to said first electrode contacting said tooth, and an indication of the intensity of said electrical stimulus is provided by said digital display means.

6. The system of claim 5 wherein said signal generating means further includes means for maintaining the duration of said pulses constant responsive to termination of said initiate signal for less than a predetermined period such that the intensity of said electrical stimulus remains constant when said first electrode loses contact with said tooth for less than a predetermined period.

7. The system of claim 5 wherein said signal generating means further includes initializing means for resetting the duration of said pulses to a predetermined value responsive to termination of said initiate signal for longer than a predetermined period such that the intensity of said electrical stimulus is initialized to a preset value by removal of said first electrode from said tooth for longer than said predetermined period.

8. The system of claim 5 wherein said contact detection means further includes means for resetting said counter means to an initial value at the commencement of said initiate signal such that said digital display means indicates the maximum value of electrical stimulus after said first electrode is removed from said tooth until said first electrode subsequently contacts a tooth.

9. The system of claim 5 wherein said probe further includes contact indication means for producing a visual indication of said initiate signal thereby producing a visual indication of electrical contact with said tooth.

10. The system of claim 5 further including means for adjusting the rate at which said pulses are generated by said signal generating means thereby adjusting the rate at which the intensity of said electrical stimulus increases responsive to said initiate signal.

11. The system of claim 5 wherein said signal generating means comprising:
   voltage controlled pulse generator means for producing a series of pulses having a pulse duration proportional to the magnitude of a pulse control signal;
   a capacitor having a pair of electrical contacts, one of which is maintained at a fixed potential;
   timer means triggered by the pulses from said voltage controlled pulse generator means for periodically generating a stimulus increase signal in response thereto; and
   means for varying the charge on said capacitor responsive to said stimulus increase signal such that the voltage across said capacitor incrementally varies with time thereby generating said pulse control signal on the other of said capacitor contacts.

12. The system of claim 5 wherein said signal processing means includes a transformer having its primary driven by said signal generating means, and its secondary connected between said first and second electrodes, said transformer having a relatively slow response time such that said transformer remains unsaturated when receiving the longest duration of said pulses such that the magnitude of the signal across said secondary is proportional to the width of said pulses.

13. The system of claim 5 further including gating means for intermittently connecting the output of said signal generating means to said signal processing means such that said electrical stimulation is produced as intermittent bursts of pulsating signals thereby allowing said pulp to reset between said bursts.

14. A system for testing the dental pulp of a tooth, comprising:
   a probe having a first electrode adapted to directly contact said tooth;
   a second electrode adapted for indirect electrical contact with said tooth;
   contact detection means for determining when said first electrode is in contact with said tooth and for generating an initiate signal in response thereto;
   control means operatively associated with said contact detection means for producing a pulse control signal having a magnitude which increases with time responsive to said initiate signal;
   oscillator means for producing a series of pulses;
   counter means for counting the number of pulses generated by said oscillator means during the period said initiate signal is being produced;
   digital display means for displaying the contents of said counter means; and
   signal processing means receiving outputs from said oscillator means and said control means for producing an electrical stimulus between said first and second electrodes having a magnitude proportional to the amplitude of said pulse control signal and a frequency corresponding to the frequency of the pulses from said oscillator means such that the intensity of said electrical stimulus increases with time responsive to said first electrode contacting said tooth, and an indication of the intensity of said electrical stimulus is provided by said digital display means.

15. The system of claim 14 wherein said processing means includes:
   a pulse transformer having its secondary connected between said first and second electrodes, and having a pair of primary leads one of which receives said pulse control signal from said control means; and
   switching means connected to the other primary lead for allowing current to flow through said primary responsive to pulses from said oscillator means such that pulses are generated across said electrodes having an amplitude proportional to the amplitude of said pulse control signal and a frequency corresponding to the frequency of pulses from said oscillator means.

16. The system of claim 14 wherein said control means further includes means for maintaining said pulse control signal constant responsive to termination of said initiate signal for less than a predetermined period such that the intensity of said electrical stimulus remains constant when said first electrode loses contact with said tooth for less then said predetermined period.

17. The system of claim 14 wherein said control means further includes initializing means for resetting said pulse control signal to a predetermined value responsive to termination of said initiate signal for longer than a predetermined period such that the intensity of said electrical stimulus is initialized to a preset value by removal of said first electrode from said tooth for longer than said predetermined period.

18. The system of claim 14 wherein said contact detection means further includes means for resetting said counter means to an initial value at the commencement of said initiate signal such that said digital display means indicates the maximum value of electrical stimulus after said first electrode is removed from said tooth until said first electrode subsequently contacts a tooth.

19. The system of claim 14 wherein said probe further includes contact indication means for producing a visual indication of said initiate signal thereby producing a visual indication of electrical contact with said tooth.

20. The system of claim 14 wherein said control means comprise:
   a capacitor having a pair of electrical contacts, one of which is maintained at a fixed potential;
   timer means triggered by the pulses from said oscillator means for periodically generating a stimulus increase signal in response thereto; and
   means for varying the charge on said capacitor responsive to said stimulus increase signal such that the voltage across said capacitor incrementally varies with time thereby generating said pulse control signal on the other of said capacitor contacts.

21. The system of claim 14 further include gating means for intermittently connecting the output of said oscillator means to said signal processing means such that said electrical stimulation is produced as intermittent bursts of pulsating signals thereby allowing said pulp to reset between said bursts.

22. A system for testing the dental pulp of a tooth, comprising:
   a probe having a first electrode adapted to directly contact said tooth;
   a second electrode adapted for indirect electrical contact with said tooth; and
   electrical stimulus means connected to said probe for producing an electrical stimulus between said first and second electrodes, said stimulus being in the form of repetitively generated burst of pulsating signals with the amplitude of said pulsating signals being relatively constant during each burst, and greater than the amplitude of the pulsating signals during the previous burst thereby allowing said pulp to reset between said bursts.

23. The system of claim 22 further including contact detection means for determining when said first electrode is in contact with said tooth, and for causing said electrical stimulus means to increase the intensity of said electrical stimulus responsive to said first electrode contacting said tooth.

24. A method of testing the dental pulp of a tooth, comprising passing an electrical stimulus through said tooth, said stimulus being in the form of repetitively generated discrete bursts of pulsating signals having sufficient duration between each discrete burst to allow said pulp to reset between said bursts.

25. The method of claim 24 wherein the amplitude of said pulsating signals is relatively constant during each burst, and greater than the amplitude of the pulsating signals during the previous burst.

* * * * *